(12) United States Patent
Deguchi

(10) Patent No.: US 11,909,941 B2
(45) Date of Patent: Feb. 20, 2024

(54) MEDICAL IMAGE PROCESSING APPARATUS AND MEDICAL OBSERVATION SYSTEM

(71) Applicant: Sony Olympus Medical Solutions Inc., Tokyo (JP)

(72) Inventor: Tatsuya Deguchi, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 381 days.

(21) Appl. No.: 16/724,307

(22) Filed: Dec. 22, 2019

(65) Prior Publication Data

US 2020/0281472 A1 Sep. 10, 2020

(30) Foreign Application Priority Data

Mar. 7, 2019 (JP) .................... 2019-042028

(51) Int. Cl.
*A61B 5/00* (2006.01)
*H04N 1/60* (2006.01)
*A61B 1/00* (2006.01)
*A61B 1/06* (2006.01)

(52) U.S. Cl.
CPC ....... *H04N 1/6077* (2013.01); *A61B 1/00009* (2013.01); *A61B 5/0071* (2013.01); *A61B 5/0077* (2013.01); *H04N 1/60* (2013.01); *A61B 1/0646* (2013.01)

(58) Field of Classification Search
CPC ... A61B 5/0077; A61B 5/0071; A61B 1/0646; H04N 1/60
See application file for complete search history.

(56) References Cited

U.S. PATENT DOCUMENTS

| | | | |
|---|---|---|---|
| 6,594,387 B1 * | 7/2003 | Pettitt | H04N 9/68 348/E9.053 |
| 9,307,120 B1 * | 4/2016 | Peng | H04N 9/04515 |
| 10,835,104 B2 * | 11/2020 | Ioka | G06T 3/4015 |

(Continued)

FOREIGN PATENT DOCUMENTS

| | | |
|---|---|---|
| JP | 2013198545 A | 10/2013 |
| JP | 2015099104 A | 5/2015 |
| JP | 2016-202726 A | 12/2016 |

*Primary Examiner* — Christopher L Cook
(74) *Attorney, Agent, or Firm* — XSENSUS LLP

(57) ABSTRACT

A medical image processing apparatus includes: a receiver configured to obtain a captured image resulting from image capture of exciting light that is shed on an observed object and is provided by way of the observed object, and of fluorescent light that is excited by the exciting light and is provided from the observed object; and an image processor configured to perform image processing on the captured image. A light receiving surface of the image sensor is provided with a color filter. The captured image includes plural pieces of first component information about colors corresponding to the spectral characteristics of the plurality of filter groups, respectively. The image processor is configured to generate second component information by combining at least two pieces of first component information, and perform color correction processing that corrects the plural pieces of first component information based on the second component information.

20 Claims, 8 Drawing Sheets

(56) References Cited

U.S. PATENT DOCUMENTS

| | | | | |
|---|---|---|---|---|
| 2002/0062061 A1* | 5/2002 | Kaneko | .............. | A61B 5/0071 |
| | | | | 600/118 |
| 2004/0215060 A1* | 10/2004 | Ueno | .............. | A61B 1/00059 |
| | | | | 600/476 |
| 2012/0127292 A1* | 5/2012 | Yamazaki | ............ | A61B 1/0646 |
| | | | | 348/E7.085 |
| 2014/0163391 A1* | 6/2014 | Koizumi | ................ | A61B 5/418 |
| | | | | 600/476 |
| 2015/0088001 A1* | 3/2015 | Lindvold | ............... | A61B 1/043 |
| | | | | 600/478 |
| 2015/0139527 A1* | 5/2015 | Ikenaga | ............... | G02B 21/365 |
| | | | | 382/133 |
| 2016/0270643 A1* | 9/2016 | Sasaki | .................. | A61B 1/0661 |
| 2017/0251915 A1* | 9/2017 | Takahashi | ............ | A61B 1/0646 |

* cited by examiner

MEDICAL IMAGE PROCESSING APPARATUS AND MEDICAL OBSERVATION SYSTEM

This application claims priority from Japanese Application No. 2019-042028, filed on Mar. 7, 2019, the contents of which are incorporated by reference herein in its entirety.

BACKGROUND

The present disclosure relates to a medical image processing apparatus and a medical observation system.

There is known a photo dynamic diagnosis apparatus for conducting photo dynamic diagnosis (PDD) that is one of methods for diagnosis of cancer in which a cancer cell is detected (refer to JP 2016-202726 A, for example).

In photo dynamic diagnosis, a photo-sensitive substance such as 5-aminolevulinic acid (which will be hereinafter referred to as 5-ALA), for example, is used. This 5-ALA is originally a natural amino acid included in a living body of an animal or a plant. The 5-ALA is taken into a cell after being administered to the inside of a body, and is bio-synthesized into protoporphyrin in mitochondria. Then, in a cancer cell, the protoporphyrin excessively accumulates. Also, the protoporphyrin excessively accumulating in the cancer cell has a light-activated property. Accordingly, the protoporphyrin emits fluorescent light (red fluorescent light in a wavelength band of 600 nm to 740 nm, for example) when being excited by exciting light (blue visible light in a wavelength band of 375 nm to 445 nm, for example). Thus, a method for diagnosis of cancer in which a cancer cell is caused to fluoresce by using a photo-sensitive substance is called photo dynamic diagnosis.

Then, a photo dynamic diagnosis apparatus described in JP 2016-202726 A includes a fluorescence imaging device that captures an image of fluorescent light provided from a photo-sensitive substance being exited by exciting light and generates a captured image of fluorescent light, and an optical filter that is provided in a preceding stage of an optical path of the fluorescence imaging device and cuts off exciting light travelling toward the fluorescence imaging device.

SUMMARY

Meanwhile, when all of exciting light travelling toward a fluorescence imaging device is cut off by an optical filter, the fluorescence imaging device captures an image of only fluorescent light provided from a photo-sensitive substance. In such a case in which an image of only fluorescent light is captured, the fluorescence imaging device generates an image that includes only a fluorescent-light component (cancer cell) and does not allow visual recognition of a background (tissues existing around the fluorescent-light component). Hence, even though a doctor or the like observes a captured image of fluorescent light, it is difficult to appreciate in what position a cancer cell is present because he may not visually recognize the background. The photo dynamic diagnosis apparatus described in JP 2016-202726 A includes an illuminating-light imaging device that captures an image of illuminating light (visible light) reflected from an observed object and generates a captured image of illuminating light, other than a fluorescence imaging device. In other words, it is possible to visually recognize the above-described background by observing a captured image of illuminating light. Nonetheless, this requires two imaging devices, and thus there is a problem of incapability of simplifying a structure.

In this regard, for a configuration using only one fluorescence imaging device, it is considered that all of exciting light travelling toward a captured image of fluorescent light is not cut off by an optical filter, but a part of the exciting light is transmitted, so that the above-described background becomes visible with an exciting-light component in the captured image of fluorescent light. However, due to variation in optical filters during manufacture, deterioration of optical filters caused by a temperature change or aging, and the like, a balance in brightness between a fluorescent-light component and an exciting-light component in a captured image of fluorescent light is not equal to a desired balance, so that the captured image of fluorescent light is not suitable for observation, in some cases.

According to one aspect of the present disclosure, there is provided a medical image processing apparatus including: a receiver configured to obtain a captured image resulting from image capture, in an image sensor, of exciting light that is shed on an observed object and is provided by way of the observed object, and of fluorescent light that is excited by the exciting light and is provided from the observed object; and an image processor configured to perform image processing on the captured image, wherein a light receiving surface of the image sensor is provided with a color filter in which a plurality of filter groups having spectral characteristics different from each other are arranged in a specific format, the captured image includes plural pieces of first component information about colors corresponding to the spectral characteristics of the plurality of filter groups, respectively, and the image processor is configured to generate second component information by combining at least two pieces of first component information out of the plural pieces of first component information about the colors, and perform color correction processing that corrects the plural pieces of first component information about the colors based on the second component information.

DETAILED DESCRIPTION

Figure 1:
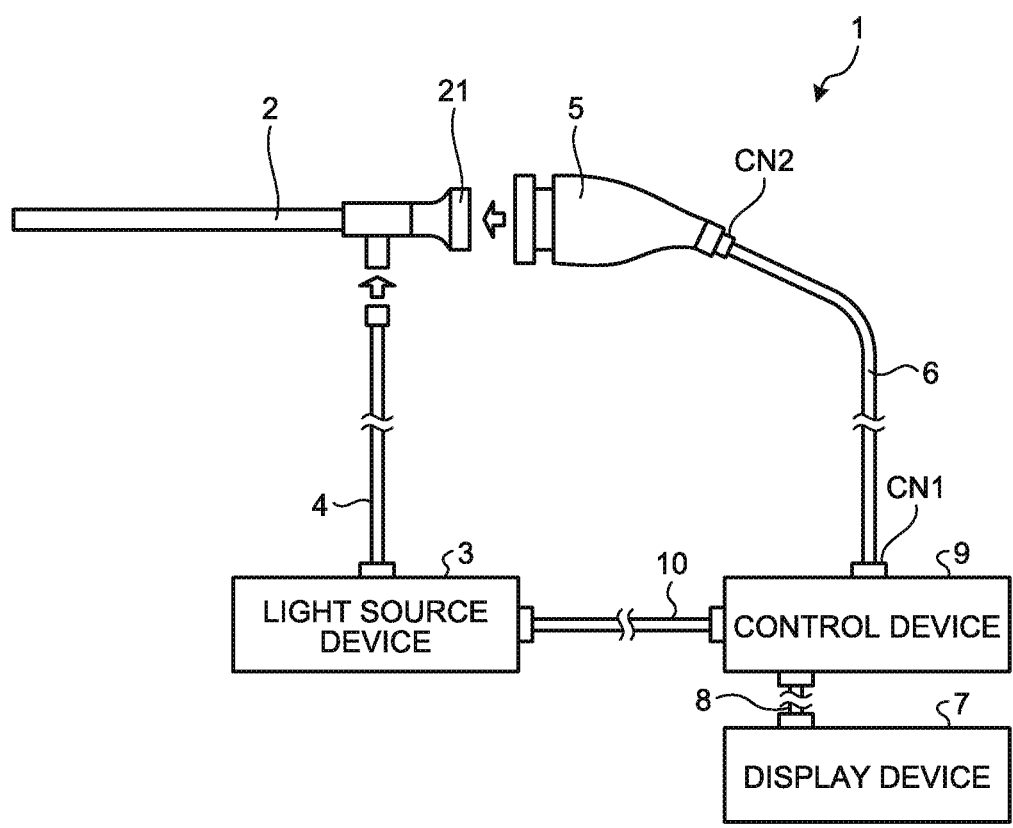
FIG. 1 is a view illustrating a configuration of a medical observation system according to a first embodiment.

Below, modes for carrying out the present disclosure (which will be hereinafter referred to as embodiments) will be described with reference to the drawings. It is noted that the present disclosure is not limited to the embodiments described below. Further, the same parts will be denoted by the same reference signs in illustration in the drawings.

First Embodiment

Outlined Configuration of Medical Observation System

FIG. 1 is a view illustrating a configuration of a medical observation system 1 according to a first embodiment.

The medical observation system 1 is used in the medical field and is a system for capturing an image of (observing) the inside of a living body (observed object) being as a subject. The medical observation system 1 includes an insertion unit 2, a light source device 3, a light guide 4, a camera head 5, a first transmission cable 6, a display device 7, a second transmission cable 8, a control device 9, and a third transmission cable 10, as illustrated in FIG. 1.

In the first embodiment, the insertion unit 2 includes a rigid endoscope. Specifically, the insertion unit 2, all of which is rigid, or a part of which is rigid while the other part is flexible, has an elongated shape, and is inserted into a living body. In the insertion unit 2, an optical system that is formed by using one lens or a plurality of lenses and collects light given from a subject is provided.

The light source device 3 produces exciting light under control of the control device 9. Then, the light source device 3 supplies the exciting light to one end of the light guide 4. In the first embodiment, the light source device 3 includes a semiconductor laser that emits exciting light in a blue wavelength band (wavelength band of 375 nm to 445 nm, for example) that excites protoporphyrin. Also, the protoporphyrin emits fluorescent light in a red wavelength band (wavelength band of 600 nm to 740 nm, for example) when being excited by the exciting light.

It is noted that although the light source device 3 is formed separately from the control device 9 in the first embodiment, the present disclosure is not limited to that and a configuration in which the light source device 3 is provided within the control device 9 may be employed.

One end of the light guide 4 is detachably connected with the light source device 3, and the other end is detachably connected with the insertion unit 2. Then, the light guide 4 transmits exciting light supplied from the light source device 3, from one end to the other end, and supplies the exciting light to the insertion unit 2. The exciting light supplied to the insertion unit 2 is emitted from a distal end of the insertion unit 2, and is shed on the inside of a living body. Exciting light that is shed on the inside of a living body and is provided by way of the living body (exciting light reflected from the inside of the living body), and fluorescent light that is emitted from protoporphyrin accumulating in a lesion portion in the living body when the protoporphyrin is excited, are collected by the optical system in the insertion unit 2. It is noted that in the following description, exciting light and fluorescent light that are collected by the optical system in the insertion unit 2 will be referred to as a subject image, for convenience in description.

The camera head 5 corresponds to an imaging device according to the present disclosure. The camera head 5 is detachably connected with a proximal end (an eyepiece unit 21 (FIG. 1)) of the insertion unit 2. Then, the camera head 5, under control of the control device 9, captures a subject image (exciting light and fluorescent light) that is collected in the insertion unit 2 and outputs an image signal (RAW signal) obtained by the capture of the subject image. The image signal is an image signal for resolution of 4K or greater, for example.

It is noted that details of a configuration of the camera head 5 will be given later.

One end of the first transmission cable 6 is detachably connected with the control device 9 via a connector CN1 (FIG. 1), and the other end is detachably connected with the camera head 5 via a connector CN2 (FIG. 1). Then, the first transmission cable 6 transmits an image signal or the like output from the camera head 5, to the control device 9, and transmits each of a control signal, a synchronizing signal, a clock, electric power, and the like, which are output from the control device 9, to the camera head 5.

It is noted that for transmission of an image signal or the like from the camera head 5 to the control device 9 via the first transmission cable 6, the image signal or the like may be transmitted in the form of a light signal or in the form of an electrical signal. The same applies also to transmission of a control signal, a synchronizing signal, and a clock from the control device 9 to the camera head 5 via the first transmission cable 6.

The display device 7 includes a display using liquid crystal, organic electro luminescence (EL), or the like, and displays an image processed in the control device 9.

One end of the second transmission cable 8 is detachably connected with the display device 7, and the other end is detachably connected with the control device 9. Then, the second transmission cable 8 transmits an image processed in the control device 9 to the display device 7.

The control device 9 corresponds to a medical image processing apparatus according to the present disclosure. The control device 9 includes a central processing unit (CPU), a field-programmable gate array (FPGA), and the like, and controls operations of the light source device 3, the camera head 5, and the display device 7 in a centralized manner.

It is noted that details of a configuration of the control device 9 will be given later.

One end of the third transmission cable 10 is detachably connected with the light source device 3, and the other end is detachably connected with the control device 9. Then, the third transmission cable 10 transmits a control signal provided from the control device 9, to the light source device 3.

Configuration of Camera Head

Next, a configuration of the camera head 5 will be described.

Figure 2:
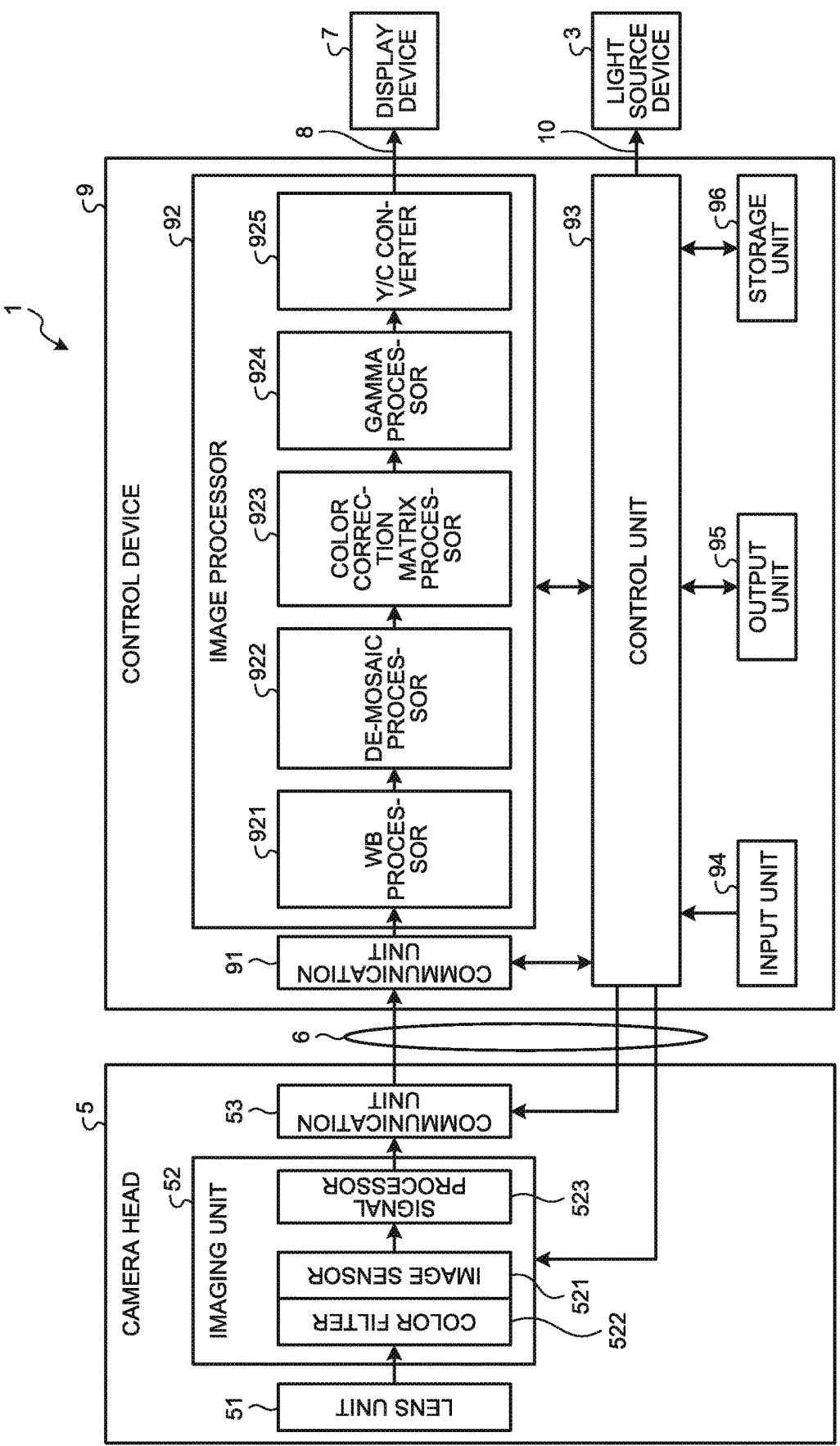
FIG. 2 is a block diagram illustrating configurations of a camera head and a control device.

FIG. 2 is a block diagram illustrating configurations of the camera head 5 and the control device 9.

It is noted that in FIG. 2, illustration of the connectors CN1 and CN2 that are interposed between the control device 9 and the first transmission cable 6, and between the camera head 5 and the first transmission cable 6, respectively, connectors that are interposed between the control device 9 and the second transmission cable 8, and between the display device 7 and the second transmission cable 8, respectively, and connectors that are interposed between the control device 9 and the third transmission cable 10, and between the light source device 3 and the third transmission cable 10, respectively, are omitted for convenience in description.

The camera head 5 includes a lens unit 51, an imaging unit 52, and a communication unit 53 as illustrated in FIG. 2.

The lens unit 51 is formed by using one lens or a plurality of lenses, and forms a subject image (exciting light and fluorescent light) that is collected in the insertion unit 2, on an imaging surface of the imaging unit 52 (image sensor 521).

The imaging unit 52 captures an image of the inside of a living body under control of the control device 9. The imaging unit 52 includes an image sensor 521, a color filter 522, and a signal processor 523 as illustrated in FIG. 2.

The image sensor 521 includes a charge coupled device (CCD), a complementary metal oxide semiconductor (CMOS), or the like, which receives light, an image of which is formed by the lens unit 51, and converts it into an electrical signal (analog signal). In the following description, a captured image that is generated by capture of a subject image (exciting light and fluorescent light) in the image sensor 521 will be referred to as a PDD image, for convenience in description.

The signal processor 523 performs signal processing on a PDD image (analog signal) generated in the image sensor 521, and outputs a PDD image (RAW signal (digital signal)).

Figure 3:
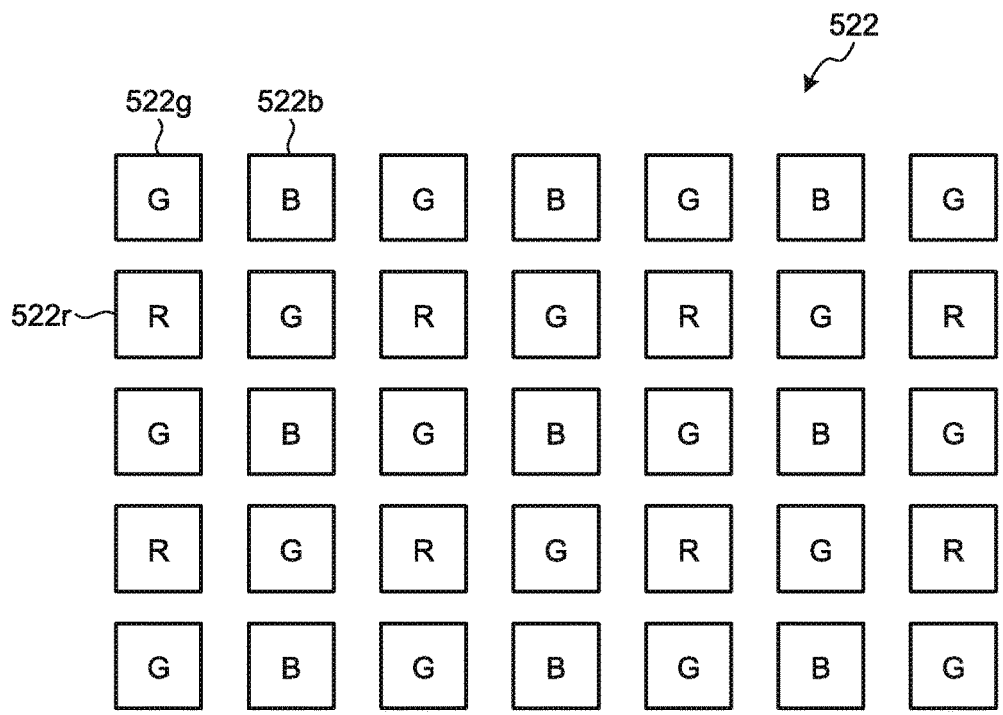
FIG. 3 is a view illustrating a color filter.

FIG. 3 is a view illustrating the color filter 522.

The color filter 522 is provided on an imaging surface (light receiving surface) of the image sensor 521, and is a color filter in which three filter groups that are grouped according to a wavelength band of light being transmitted (R (red), G (green), and B (blue)) are arranged in a specific format (Bayer array, for example).

Specifically, as illustrated in FIG. 3, the color filter 522 includes an R filter group 522r that transmits mainly light in an R wavelength band, a B filter group 522b that transmits mainly light in a B wavelength band, and a first G filter group (arranged in the same column as the R filter group 522r) that transmits mainly light in a G wavelength band, and a second G filter group (arranged in the same column as the B filter group 522b) that transmits mainly light in a G wavelength band. It is noted that in FIG. 3, the first and second G filter groups are collectively referred to as G filter groups 522g. Also, in FIG. 3, the R filter group 522r is marked with a character "R", the G filter group 522g is marked with a character "G", and the B filter group 522b is marked with a character "B".

Figure 4:
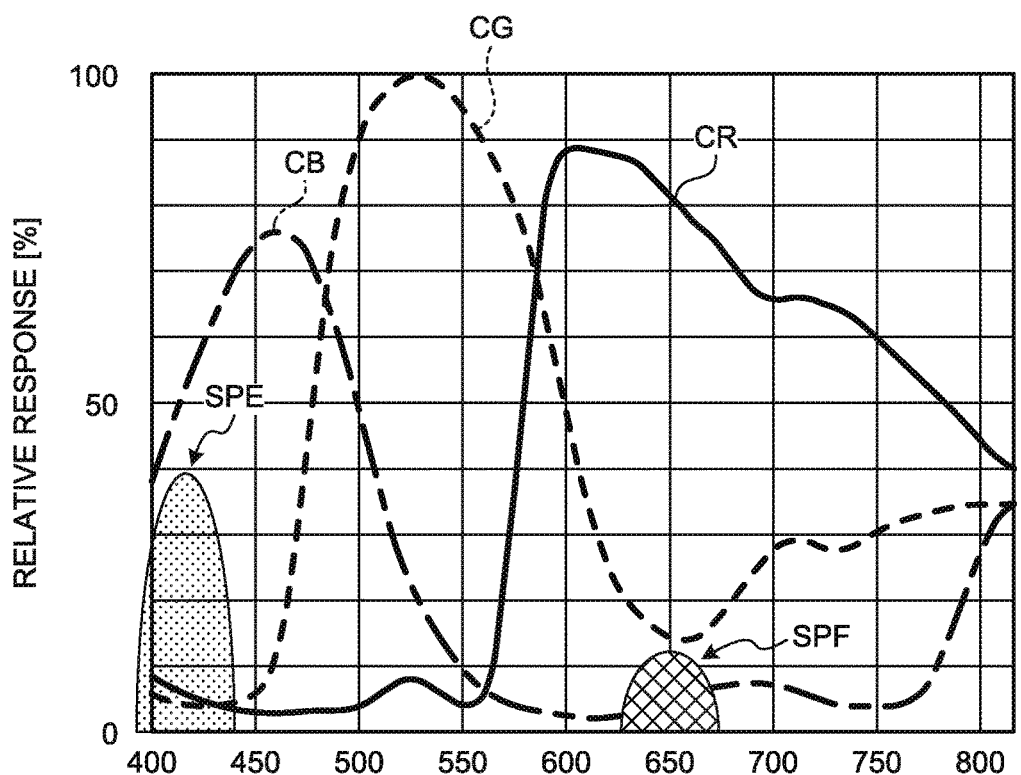
FIG. 4 is a view illustrating spectral characteristics of the color filter.

FIG. 4 is a view illustrating spectral characteristics of the color filter 522. Specifically, in FIG. 4, spectral characteristics of the R filter group 522r are indicated by a curve CR, spectral characteristics of the G filter group 522g are indicated by a curve CG, and spectral characteristics of the B filter group 522b are indicated by a curve CB. Further, in FIG. 4, also a spectrum SPE of exciting light and a spectrum SPF of fluorescent light are illustrated.

As illustrated in FIG. 4, the R filter group 522r transmits mainly light in an R wavelength band including fluorescent light, and also transmits a part of exciting light. Thus, in a PDD image generated in the imaging unit 52, pixel data (which corresponds to first component information according to the present disclosure and will be hereinafter referred to as an r value) of a pixel for the R filter group 522r is a combination of a fluorescent-light component and an exciting-light component. Also, the G filter group 522g transmits mainly light in a G wavelength band, and also transmits a part of fluorescent light and exciting light. Thus, in a PDD image, pixel data (which corresponds to the first component information according to the present disclosure and will be hereinafter referred to as a g value) of a pixel for the G filter group 522g is a combination of a fluorescent-light component and an exciting-light component. Further, the B filter group 522b transmits mainly light in a B wavelength band including exciting light, and also transmits a part of fluorescent light. Thus, in a PDD image, pixel data (which corresponds to the first component information according to the present disclosure and will be hereinafter referred to as a b value) of a pixel for the B filter group 522b is a combination of a fluorescent-light component and an exciting-light component.

Figure 5:
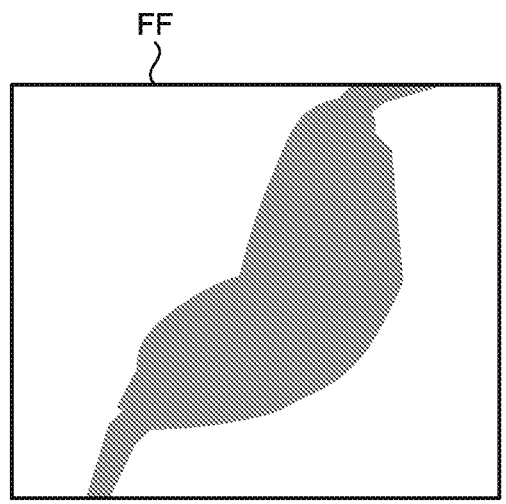
FIG. 5 is a view illustrating one example of a PDD image.

FIG. 5 is a view illustrating one example of a PDD image FF. Specifically, in FIG. 5, an area ArF expressed in gray corresponds to a lesion portion where protoporphyrin excessively accumulates, and is an area composed mainly of a fluorescent-light component.

In the PDD image FF generated in the imaging unit 52, a background (an area expressed in white in the PDD image FF) around the area ArF is composed mainly of an exciting-light component. In the first embodiment, the imaging unit 52 is not provided with an optical filter that cuts off exciting light travelling toward the image sensor 521. That is, a large amount of exciting light reflected from an observed object is incident upon the image sensor 521. Accordingly, the above-described background is brighter than the area ArF, which makes it difficult to visually recognize the area ArF.

Hence, in the first embodiment, by image processing performed by the control device 9 described later, a fluorescent-light component and an exciting-light component that are combined with each other in an r value, a g value, and a b value are separated, so that a balance in brightness between the area ArF and the above-described background becomes equal to a desired balance.

The communication unit 53 functions as a transmitter that transmits a PDD image (RAW signal (digital signal)) output from the imaging unit 52, to the control device 9 via the first transmission cable 6. The communication unit 53 includes, for example, a high-speed serial interface that transmits/receives a PDD image to/from the control device 9 at a transmission rate of 1 Gbps or higher via the first transmission cable 6.

Configuration of Control Device

Next, a configuration of the control device 9 will be described with reference to FIG. 2.

As illustrated in FIG. 2, the control device 9 includes a communication unit 91, an image processor 92, a control unit 93, an input unit 94, an output unit 95, and a storage unit 96.

The communication unit 91 functions as a receiver that receives a PDD image (RAW signal (digital signal)) output from the camera head 5 (the communication unit 53) via the first transmission cable 6. The communication unit 91 includes a high-speed serial interface that transmits/receives a PDD image to/from the communication unit 53 at a transmission rate of 1 Gbps or higher, for example.

The image processor 92 processes a PDD image (RAW signal (digital signal)) that is sequentially output from the camera head 5 (the communication unit 53) and is received by the communication unit 91, under control of the control unit 93. The image processor 92 includes a WB processor 921, a de-mosaic processor 922, a color correction matrix processor 923, a gamma processor 924, a Y/C converter 925, as illustrated in FIG. 2.

The WB processor 921 performs white-balance (WB) processing in which each of an r value, a g value, and a b value in a PDD image (RAW signal (digital signal)) is multiplied by a specific gain.

The de-mosaic processor 922 performs de-mosaic processing in which a pixel value (R (r value), G (g value), B (b value)) of an r value, a g value, and a b value is given to each pixel by interpolation, on a PDD image provided after WB processing.

The color correction matrix processor 923 performs color correction matrix processing (which corresponds to color correction processing according to the present disclosure) on a PDD image provided after de-mosaic processing.

Specifically, the color correction matrix processor 923 corrects a pixel value (R, G, B) of each pixel into a pixel value ($R_m$, $G_m$, $B_m$) using the following equation (1). It is noted that in the equation (1), $M_{col}$ represents a color correction matrix. The equation (1) represents a case in which a 3*8-matrix is employed as the color correction matrix $M_{col}$. A method of calculating the color correction matrix will be described later. Also, $M_{input}$ represents an input matrix by which the color correction matrix $M_{col}$ is multiplied. In the equation (1), the input matrix $M_{input}$ includes each pixel value (R, G, B) as a matrix element, and in addition, includes each of "R*G", "G*B", "R*B", and "R*G*B" as a matrix element.

In other words, the input matrix $M_{input}$ includes second component information ("R*B", "G*B", "R*B", and "R*G*B") that is a combination of at least two pieces of the first component information out of three pieces of the first component information (a pixel value (R, G, B)), as a matrix element.

In this regard, in view of a finding that the curve CR extends across not only an R wavelength band, but also a G wavelength band, a matrix element "R*G" that is obtained by multiplication of R and G included in a pixel value (R, G, B) is a matrix element that indicates what amount of components for light in a G wavelength band is included in R (r value). Also, in view of a finding that the curve CG extends across not only a G wavelength band, but also an R wavelength band, the matrix element "R*G" is a matrix element that indicates what amount of components for light in an R wavelength band is included in G (g value).

Also, in view of a finding that the curve CG extends across not only a G wavelength band, but also a B wavelength band, a matrix element "G*B" that is obtained by multiplication of G and B included in a pixel value (R, G, B) is a matrix element that indicates what amount of components for light in a B wavelength band is included in G (g value). Also, in view of a finding that the curve CB extends across not only a B wavelength band, but also a G wavelength band, the matrix element "G*B" is a matrix element that indicates what amount of components for light in a G wavelength band is included in B (b value).

Further, in view of a finding that the curve CR extends across not only an R wavelength band, but also a B wavelength band, a matrix element "R*B" that is obtained by multiplication of R and B included in a pixel value (R, G, B) is a matrix element that indicates what amount of components for light in a B wavelength band is included in R (r value). Also, in view of a finding that the curve CB extends across not only a B wavelength band, but also an R wavelength band, the matrix element "R*B" is a matrix element that indicates what amount of components for light in an R wavelength band is included in B (b value).

Moreover, in view of a finding that the curve CR extends across not only an R wavelength band, but also G and B wavelength bands, a matrix element "R*G*B" that is obtained by multiplication of all of R, G, and B included in a pixel value (R, G, B) is a matrix element that indicates what amount of components for light in G and B wavelength bands is included in R (r value). Also, in view of a finding that the curve CG extends across not only a G wavelength band, but also R and B wavelength bands, the matrix element "R*G*B" is a matrix element that indicates what amount of components for light in R and B wavelength bands is included in G (g value). Further, in view of a finding that the curve CB extends across not only a B wavelength band, but also R and G wavelength bands, the matrix element "R*G*B" is a matrix element that indicates what amount of components for light in R and G wavelength bands is included in B (b value).

$$\begin{pmatrix} R_m \\ G_m \\ B_m \end{pmatrix} = M_{col} * M_{input} \quad (1)$$

$$M_{col} = \begin{pmatrix} a & b & c & d & e & f & g & h \\ i & j & k & l & m & n & o & p \\ q & r & s & t & u & v & w & x \end{pmatrix}$$

$$M_{input} = \begin{pmatrix} R \\ G \\ B \\ R*G \\ G*B \\ R*B \\ R*G*B \\ 1 \end{pmatrix}$$

Then, the color correction matrix processor 923 calculates the input matrix $M_{input}$ from a pixel value (R, G, B) of each pixel and multiplies the color correction matrix $M_{col}$ by the calculated input matrix $M_{input}$, to calculate a corrected pixel value ($R_m$, $G_m$, $B_m$).

It is noted that although a case where a 3*8-color correction matrix $M_{col}$ is employed is described as an example in the equation (1), the present disclosure is not limited to that. For example, a 3*7-color correction matrix $M_{col}$ represented by the following equation (2), a 3*6-color correction matrix $M_{col}$ represented by the following equation (3), or a 3*5-color correction matrix $M_{col}$ represented by the following equation (4) may be employed. The input matrix $M_{input}$ represented by the equation (2) is identical to the input matrix $M_{input}$ represented by the equation (1) in which a matrix element "R*G*B" is omitted. While three input matrices $M_{input}$ are cited in the equation (3), any of the three input matrices $M_{input}$ may be used. Each of the three input matrices $M_{input}$ is identical to the input matrix $M_{input}$ represented by the equation (2) in which one of a matrix element "R*G", a matrix element "G*B", and a matrix element "R*B" is omitted. While three input matrices $M_{input}$ are cited in the equation (4), any of the three input matrices $M_{input}$ may be used. Each of the three input matrices $M_{input}$ is identical to the input matrix $M_{input}$ represented by the equation (2) in which any two of a matrix element "R*G", a matrix element "G*B", and a matrix element "R*B" are omitted.

$$M_{col} = \begin{pmatrix} a & b & c & d & e & f & g \\ h & i & j & k & l & m & n \\ o & p & q & r & s & t & u \end{pmatrix} \quad (2)$$

$$M_{input} = \begin{pmatrix} R \\ G \\ B \\ R*G \\ G*B \\ R*B \\ 1 \end{pmatrix}$$

$$M_{col} = \begin{pmatrix} a & b & c & d & e & f \\ g & h & i & j & k & l \\ m & n & o & p & q & r \end{pmatrix} \quad (3)$$

$$M_{input} = \begin{pmatrix} R \\ G \\ B \\ R*G \\ G*B \\ 1 \end{pmatrix}$$

$$M_{input} = \begin{pmatrix} R \\ G \\ B \\ R*G \\ R*B \\ 1 \end{pmatrix}$$

$$M_{input} = \begin{pmatrix} R \\ G \\ B \\ G*B \\ R*B \\ 1 \end{pmatrix}$$

$$M_{col} = \begin{pmatrix} a & b & c & d & e \\ f & g & h & i & j \\ k & l & m & n & o \end{pmatrix} \quad (4)$$

$$M_{input} = \begin{pmatrix} R \\ G \\ B \\ R*G \\ 1 \end{pmatrix}$$

$$M_{input} = \begin{pmatrix} R \\ G \\ B \\ G*B \\ 1 \end{pmatrix}$$

$$M_{input} = \begin{pmatrix} R \\ G \\ B \\ R*B \\ 1 \end{pmatrix}$$

The gamma processor 924 performs gamma processing (γ correction) on a PDD image provided after color correction matrix processing.

The Y/C converter 925 performs Y/C conversion that converts a PDD image (RGB signal) provided after gamma processing, into a luminance signal and a color-difference signal (Y, $C_B$/$C_R$ signal). Then, the image processor 92 outputs a PDD image provided after Y/C conversion, to the display device 7 via the second transmission cable 8. As a result of this, the display device 7 displays the PDD image.

The control unit 93 is formed by using a CPU, a FPGA, and the like, for example, and outputs a control signal via the first to third transmission cables 6, 8, and 10, to control operations of the light source device 3, the camera head 5, and the display device 7, and also control operations of the control device 9 as a whole.

The input unit 94 is formed by using an operating device such as a mouse, a keyboard, a touch panel, or the like, and accepts a user operation performed by a user such as a doctor. Then, the input unit 94 outputs an operation signal responsive to the user operation, to the control unit 93.

The output unit 95 is formed by using a speaker, a printer, or the like, and outputs a variety of information.

In the storage unit 96, a program to be executed by the control unit 93, information necessary for processing in the control unit 93, and the like, are stored.

Method of Calculating a Color Correction Matrix

Next, a method of calculating the above-described color correction matrix $M_{col}$ will be described.

Figure 6:
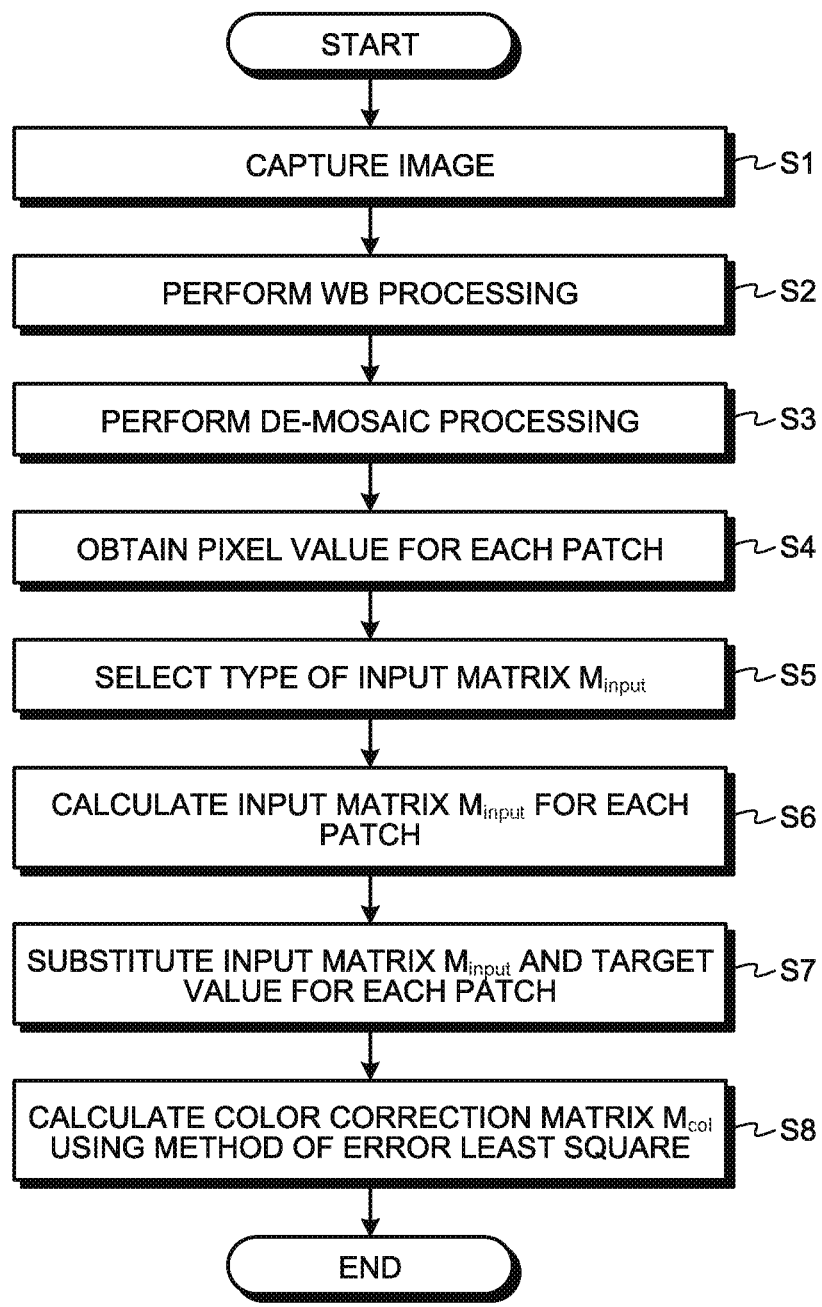
FIG. 6 is a flow chart illustrating a method of calculating a color correction matrix.
Figure 7:
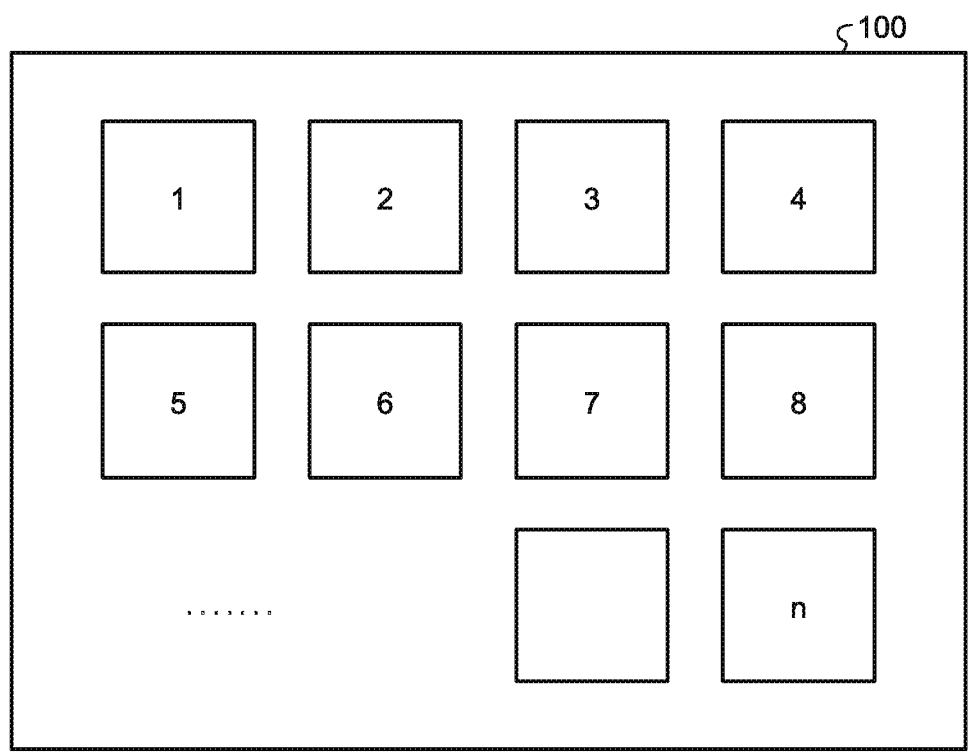
FIG. 7 is a view illustrating a color patch used in the method of calculating a color correction matrix illustrated in FIG. 6.

FIG. 6 is a flow chart illustrating a method of calculating the color correction matrix $M_{col}$. FIG. 7 is a view illustrating a color patch 100 used in the method of calculating a color correction matrix illustrated in FIG. 6.

First, while the color patch 100 (FIG. 7) is being irradiated with exciting light produced in the light source device 3, an operator causes the imaging unit 52 to capture an image of the color patch 100 (step S1).

Meanwhile, the color patch 100 is formed of a Macbeth color chart or the like, for example, in which color samples (which will be hereinafter referred to as patches) different from each other are arranged. It is noted that in FIG. 7, the patches are marked with symbols 1 to n for convenience in description.

After the step S1, an operator performs WB processing (step S2) and de-mosaic processing (step S3) on a PDD image (RAW signal (digital signal)) generated in the imaging unit 52, with the use of the image processor 92, to thereby obtain a pixel value (R, G, B) of each of the patches 1 to n (step S4).

After the step S4, an operator selects a type of the input matrix $M_{input}$ (step S5).

Specifically, in calculating a 3*8-color correction matrix $M_{col}$, an operator selects the input matrix $M_{input}$ of the equation (1). Also, in calculating a 3*7-color correction matrix $M_{col}$, an operator selects the input matrix $M_{input}$ of the equation (2). Further, in calculating a 3*6-color correction matrix $M_{col}$, an operator selects any of the three input matrices $M_{input}$ of the equation (3). Moreover, in calculating a 3*5-color correction matrix $M_{col}$, an operator selects any of the three input matrices $M_{input}$ of the equation (4).

After the step S5, an operator calculates each input matrix $M_{input}$ that is selected in the step S5, from each of respective pixel values (R, G, B) of the patches 1 to n, the pixel values being obtained in the step S4 (step S6). That is, by the step S6, the input matrix $M_{input}$ is calculated for each of the patches 1 to n.

After the step S6, an operator substitutes the input matrix $M_{input}$ calculated for each of the patches 1 to n in the step S6 and a target value ($R_{target}$, $G_{target}$, $B_{target}$) for each of the patches 1 to n, into the following equation (5) (step S7). That is, by the step S7, the equation (5) in which the color correction matrix $M_{col}$ is a variable is produced for each of the patches 1 to n.

$$\begin{pmatrix} R_{target} \\ G_{target} \\ B_{target} \end{pmatrix} = M_{col} * M_{input} \quad (5)$$

Here, the target value ($R_{target}$, $G_{target}$, $B_{target}$) for each of the patches 1 to n is an ideal pixel value for each of the patches 1 to n, and for example, a pixel value for each of the patches 1 to n in a PDD image that is captured in a state in which an optical filter that cuts off a part of exciting light travelling toward the image sensor 521 is provided in the imaging unit 52, may be employed.

After the step S7, an operator, with the use of the method of error least square, calculates the color correction matrix $M_{col}$ from the equation (5) in which the color correction matrix $M_{col}$ is a variable, the equation (5) being produced for each of the patches 1 to n in the step S7 (step S8).

The above-described first embodiment produces the following effects.

The control device 9 according to the first embodiment combines at least two pieces of the first component information out of three pieces of the first component information (pixel value (R, G, B)), to generate the second component information ("R*B", "G*B", "R*B", "R*G*B"), and performs color correction processing that corrects the three pieces of first component information based on the second component information. More specifically, the control device 9 multiplies the color correction matrix $M_{col}$ by the input matrix $M_{input}$ including each of three pieces of the first component information and the second component information as a matrix element, to thereby perform color correction processing that corrects three pieces of first component information.

Accordingly, a fluorescent-light component and an exciting-light component that are combined with each other in an r value, a g value, and a b value are separated by color correction processing, so that a balance in brightness between the area ArF (fluorescent-light component) and a background (exciting-light component) in the PDD image FF may be made equal to a desired balance.

Therefore, for a configuration of the medical observation system 1, a configuration of a single-plate type including only one image sensor 521 may be used, and a structure may be simplified because there is no need of using an optical filter for cutting off exciting light. Also, the control device 9 may make a balance in brightness between the area ArF and a background in the PDD image FF equal to a desired balance, so that an image suitable for observation may be generated.

Second Embodiment

Next, a second embodiment will be described.

In the following description, the same components as those in the above-described first embodiment will be denoted by the same reference signs, and detailed description thereof will be omitted or simplified.

In the above-described first embodiment, the present disclosure is applied to the medical observation system 1 using a rigid endoscope (insertion unit 2).

In contrast thereto, in the second embodiment, the present disclosure is applied to a medical observation system using a so-called videoscope in which an imaging unit is provided at a distal end of an insertion unit.

Figure 8:
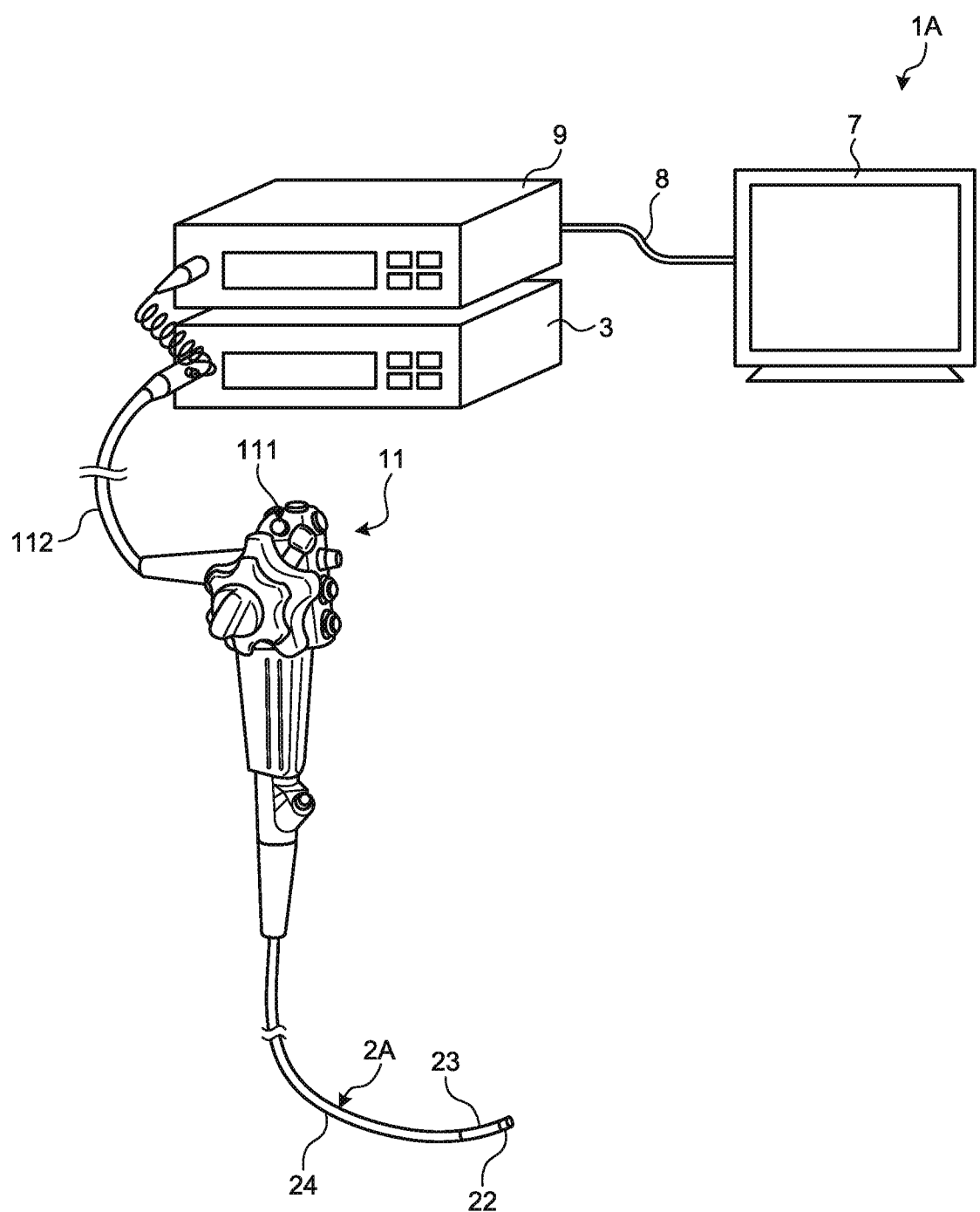
FIG. 8 is a view illustrating a configuration of a medical observation system according to a second embodiment.

FIG. 8 is a view illustrating a configuration of a medical observation system 1A according to the second embodiment.

As illustrated in FIG. 8, the medical observation system 1A according to the second embodiment includes an endoscope 11 that captures an in-vivo image of an observed region through insertion of an insertion unit 2A into a living body and outputs an image signal, a light source device 3 that produces illuminating light emitted from a distal end of the endoscope 11, a control device 9 that processes an image signal output from the endoscope 11, and a display device 7 that is connected with the control device 9 via a second transmission cable 8 and displays a PDD image that is processed in the control device 9.

As illustrated in FIG. 8, the endoscope 11 includes the insertion unit 2A that has flexibility and an elongated shape, an operating unit 111 that is connected with a proximal-end side of the insertion unit 2A and accepts various kinds of operations, and a universal code 112 that extends from the operating unit 111 in a direction different from a direction in which the insertion unit 2A extends, and incorporates various kinds of cables being connected with the light source device 3 and the control device 9.

As illustrated in FIG. 8, the insertion unit 2A includes a distal end 22, a bending unit 23 that is connected with a proximal-end side of the distal end 22 and is formed of a plurality of bending pieces so as to be bendable, and a flexible tube unit 24 that is connected with a proximal-end side of the bending unit 23 and has flexibility and a great length.

Then, inside the distal end 22, a configuration that is substantially similar to the imaging unit 52 described above in the first embodiment is incorporated though specific illustration thereof is omitted. Also, inside the operating unit 111, a configuration that is substantially similar to the communication unit 53 described above in the first embodiment is incorporated though specific illustration thereof is omitted. Then, a PDD image captured in the distal end 22 (imaging unit) is output to the control device 9 via the operating unit 111 and the universal code 112.

The same effects as those in the above-described first embodiment are produced even in a case in which a flexible endoscope (endoscope 11) is used, like a case in the above-described second embodiment.

Third Embodiment

Next, a third embodiment will be described.

In the following description, the same components as those in the above-described first embodiment will be denoted by the same reference signs, and detailed description thereof will be omitted or simplified.

In the above-described first embodiment, the present disclosure is applied to the medical observation system 1 using a rigid endoscope (insertion unit 2).

In contrast thereto, in the third embodiment, the present disclosure is applied to a medical observation system using a surgical microscope that captures an image of a predetermined field of view of the inside of a subject (the inside of a living body) or a surface of a subject (a surface of a living body) while enlarging it.

Figure 9:
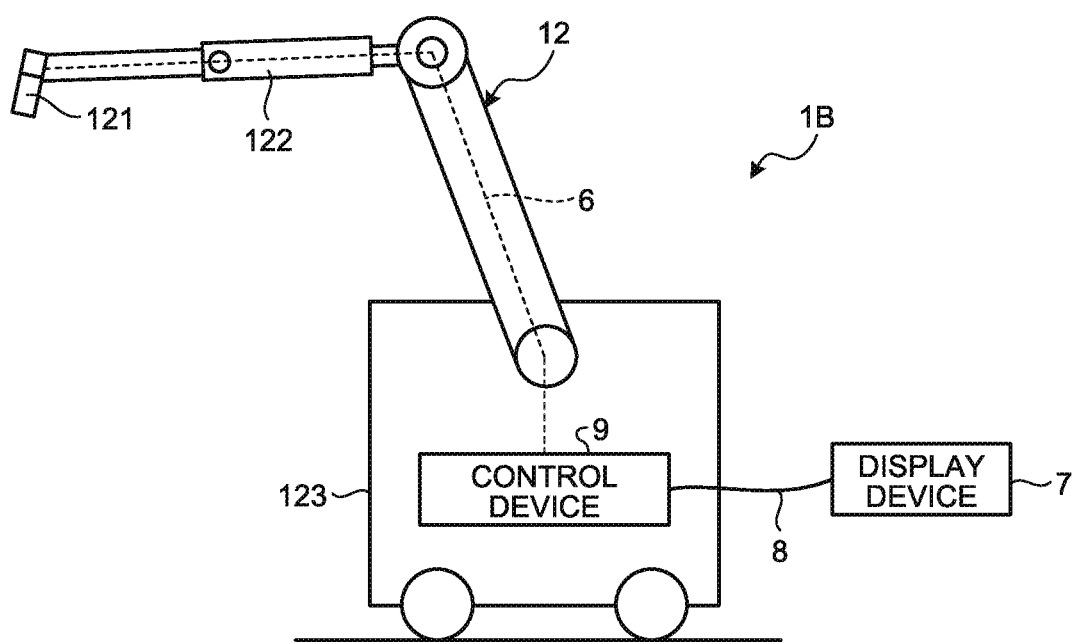
FIG. 9 is a view illustrating a configuration of a medical observation system according to a third embodiment.

FIG. 9 is a view illustrating a configuration of a medical observation system 1B according to the third embodiment.

As illustrated in FIG. 9, the medical observation system 1B according to the third embodiment includes a surgical microscope 12 that captures an image of a subject and outputs a PDD image, a control device 9 that processes a PDD image output from the surgical microscope 12, and a display device 7 that is connected with the control device 9 via a second transmission cable 8 and displays a PDD image processed in the control device 9.

As illustrated in FIG. 9, the surgical microscope 12 includes a microscope unit 121 that captures an image of a minute region of a subject while enlarging it and outputs a PDD image, a support unit 122 that is connected with a proximal end of the microscope unit 121 and includes an arm that supports the microscope unit 121 in such a manner that the microscope unit 121 may rotate, and a base unit 123 that supports a proximal end of the support unit 122 in such a manner that the support unit 122 may rotate, and is movable on a floor surface.

Then, as illustrated in FIG. 9, the control device 9 is placed in the base unit 123. Also, in the base unit 123, a light source device 3 that produces exciting light to be emitted from the surgical microscope 12 toward a subject is placed though specific illustration thereof is omitted.

It is noted that there may be provided a configuration in which the base unit 123 supports the support unit 122 while being fixed to a ceiling, a wall surface, or the like, instead of being movably provided on a floor surface.

In the microscope unit 121, configurations that are substantially similar to the imaging unit 52 and the communication unit 53 described above in the first embodiment are incorporated through specific illustration thereof is omitted. Then, a PDD image captured in the microscope unit 121 (imaging unit) is output to the control device 9 via a first transmission cable 6 wired along the support unit 122.

The same effects as those in the above-described first embodiment are produced even in a case where the surgical microscope 12 is used, like a case in the above-described third embodiment.

Other Embodiments

While modes for carrying out the present disclosure have been described hereinabove, the present disclosure should not be limited only to the above-described first to third embodiments.

Though the medical image processing apparatus according to the present disclosure is mounted in the medical observation system 1 (1A, 1B) for conducting photo dynamic diagnosis in the above-described first to third embodiments, the present disclosure is not limited to that. Specifically, the medical image processing apparatus according to the present disclosure may be mounted in a medical observation system in which a wavelength band of exciting light or fluorescent light is different from a wavelength band described in the above-described first to third embodiments and an observation technique different from the photo dynamic diagnosis is adopted.

Though there is provided a configuration in which de-mosaic processing is performed between WB processing and color correction matrix processing in the above-described first to third embodiments, the present disclosure is not limited to that. The de-mosaic processing may be performed before color correction matrix processing or before WB processing as long as the de-mosaic processing is performed before gamma processing. Also, the image processor 92 may be configured such that the respective processors 921 to 925 are placed in an order different from that illustrated in FIG. 2 in the first to third embodiments.

Though component information obtained by multiplication of at least two pieces of the first component information out of three pieces of the first component information (pixel value (R, G, B)) is used as the second component information that is to be included as a matrix element in the input matrix $M_{input}$ in the above-described first to third embodiments, the present disclosure is not limited to that. As long as component information obtained by a combination of at least two pieces of the first component information is used, the component information may be used as the other component information.

Though each of the filter groups 522r, 522g, and 522b forming the color filter 522 is configured so as to serve as a filter group that transmits mainly light in an R, G, or B wavelength band in the above-described first to third embodiments, the present disclosure is not limited to that. A plurality of filter groups according to the present disclosure may be configured so as to serve not only as the filter groups 522r, 522g, and 522b for the combinations of colors described above in the first to third embodiments, but also as filter groups for the other combinations of colors, as long as the plurality of filter groups have spectral characteristics different from each other.

A part of components of the camera head 5 or a part of components of the control device 9 may be provided in the connector CN1 or the connector CN2, for example, in the above-described first to third embodiments.

With the medical image processing apparatus and the medical observation system according to the present disclosure, it is possible to generate an image suitable for observation while simplifying a structure.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing apparatus comprising:
   an image sensor configured to capture an image of an observed object illuminated with exciting light, the captured image including fluorescent light output from the observed object illuminated by the exciting light and exciting light reflected by the observed object illuminated by the exciting light; and
   an image processor configured to perform image processing on the captured image, wherein
   a light receiving surface of the image sensor is provided with a color filter in which a plurality of filter groups having spectral characteristics different from each other are arranged in a specific format,
   the plurality of filter groups together transmitting white light,
   each filter group of the plurality of filter groups transmits the exciting light and the fluorescent light,
   the captured image includes plural pieces of first component information about colors corresponding to the spectral characteristics of the plurality of filter groups, respectively, and
   the image processor is configured to
      generate second component information by using at least one combination of two different pieces of first component information out of the plural pieces of first component information about the colors obtained by multiplication of the two different pieces of first component information, and
      perform color correction processing that corrects the plural pieces of first component information about the colors by multiplying an input matrix containing each of the plural pieces of first component information and the second component information as matrix elements by a color correction matrix so that a brightness of an exciting light component of the captured image and a brightness of a fluorescent light component of the captured image equals a predetermined balance.

2. The medical image processing apparatus according to claim 1, wherein the input matrix includes each of the plural pieces of first component information about the colors as a matrix element.

3. The medical image processing apparatus according to claim 1, wherein
the plurality of filter groups are three filter groups that are grouped according to a wavelength band for red, green, or blue, and
the captured image includes the first component information about red, green, and blue corresponding to spectral characteristics of the three filter groups, respectively.

4. The medical image processing apparatus according to claim 1, wherein the exciting light is light that excites protoporphyrin.

5. The medical image processing apparatus according to claim 1, wherein the image processor is further configured to
generate the second component information by using at least two different combinations of two different pieces of the first component information out of the plural pieces of the first component information about the colors.

6. The medical image processing apparatus according to claim 1, wherein the image processor is configured to calculate the color correction matrix from a plurality of color patches imaged by the image sensor while the observed object is illuminated by the exciting light, each color patch in the plurality of color patches being different from each other and a number of color patches is greater than a number of filter groups.

7. The medical image processing apparatus according to claim 6, wherein the image processor is configured to determine the color correction matrix for each color patch of the plurality of color patches based on an ideal pixel value for that color patch.

8. The medical image processing apparatus according to claim 6, wherein a size of the color correction matrix is determined based on a size of the input matrix selected by an operator.

9. The medical image processing apparatus according to claim 8, wherein the image processor is configured to generate third component information by using a combination of all pieces of first component information out of the plural pieces of first component information and the third component information is a matrix element of the input matrix.

10. The medical image processing apparatus according to claim 6, wherein each color patch extends continuously over a region having at least one of each of the filter groups.

11. A medical observation system comprising:
a light source device configured to emit exciting light to be incident on an observed object;
an imaging device including:
an image sensor configured to generate a captured image from the observed object illuminated with exciting light, the captured image including fluorescent light output from the observed object illuminated by the exciting light and exciting light reflected by from the observed object; and
a color filter in which a plurality of filter groups having spectral characteristics different from each other are arranged in a specific format, the color filter being provided in a light receiving surface of the image sensor, wherein the color filter transmits light in a wavelength region larger than and overlapping the exciting light and the fluorescent light; and
an image processor configured to
generate second component information by using at least one combination of two different pieces of first component information out of the plural pieces of first component information about the colors obtained by multiplication of the two different pieces of first component information, and
perform color correction processing that corrects the plural pieces of first component information about the colors by multiplying an input matrix containing each of the plural pieces of first component information and the second component information as matrix elements by a color correction matrix so that a brightness of an exciting light component of the captured image and a brightness of a fluorescent light component of the captured image equals a predetermined balance.

12. A medical image processing method comprising:
obtaining an image from an observed object illuminated with exciting light using an image sensor, the image including fluorescent light output from the observed object illuminated by the exciting light and exciting light reflected by the observed object illuminated by the exciting light, from a light receiving surface of the image sensor provided with a color filter in which a plurality of filter groups having spectral characteristics different from each other are arranged in a specific format, each filter group of the plurality of filter groups transmits the exciting light and the fluorescent light and the plurality of filter groups together transmitting white light;
generating first component information about colors corresponding to the spectral characteristics of the plurality of filter groups, respectively, that includes plural pieces of first component information, and
generating second component information by using at least one combination of two different pieces of first component information out of the plural pieces of first component information about the colors obtained by multiplying the two different pieces of first component information, and
color correction processing that corrects the plural pieces of first component information about the colors by multiplying an input matrix containing each of the plural pieces of first component information and the second component information as matrix elements by a color correction matrix so that a brightness of an exciting light component of the image and a brightness of a fluorescent light component of the image equals a predetermined balance.

13. The medical image processing method according to claim 12, further comprising calculating the color correction matrix from a plurality of color patches imaged by the image sensor while the observed object is illuminated by the exciting light, each color patch in the plurality of color patches being different from each other and a number of color patches is greater than a number of filter groups.

14. The medical image processing method according to claim 13, wherein a size of the color correction matrix is determined based on a size of the input matrix selected by an operator.

15. The medical image processing method according to claim 13, further comprising determining the color correction matrix for each color patch of the plurality of color patches based on an ideal pixel value for that color patch.

16. The medical image processing method according to claim 12, further comprising generating third component information by using a combination of all pieces of first component information out of the plural pieces of first component information, wherein the third component information is a matrix element of the input matrix.

17. A non-transitory computer readable storage device having computer readable instructions that when executed by circuitry cause the circuitry to:
   generate first component information about colors corresponding to spectral characteristics of a plurality of filter groups, respectively, that includes plural pieces of first component information, in an image obtained by illuminating an observed object with exciting light using an image sensor, the image including fluorescent light output from the observed object illuminated by the exciting light and exciting light reflected by the observed object illuminated by the exciting light, the plurality of filter groups having spectral characteristics different from each other are arranged in a specific format on a light receiving surface of the image sensor, wherein the plurality of filter groups together transmit white light and each filter group of the plurality of filter groups transmits the exciting light and the fluorescent light;
   generate second component information by using at least one combination of two different pieces of first component information out of the plural pieces of first component information about the colors obtained by multiplication of the two different pieces of first component information, and
   perform color correction processing that corrects the plural pieces of first component information about the colors by multiplying an input matrix containing each of the plural pieces of first component information and the second component information as matrix elements by a color correction matrix so that a brightness of an exciting light component of the image and a brightness of a fluorescent light component of the image equals a predetermined balance.

18. The non-transitory computer readable storage device according to claim 17, wherein the computer readable instructions cause the circuitry to calculate the color correction matrix from a plurality of color patches imaged while the observed object is illuminated by the exciting light, each color patch in the plurality of color patches being different from each other and a number of color patches is greater a number of filter groups.

19. The non-transitory computer readable storage device according to claim 18, wherein a size of the color correction matrix is determined based on a size of the input matrix selected by an operator.

20. The non-transitory computer readable storage device according to claim 17, wherein the computer readable instructions cause the circuitry to generate third component information by using a combination of all pieces of first component information out of the plural pieces of first component information and the third component information is a matrix element of the input matrix.

* * * * *